United States Patent
Koganezawa et al.

[11] Patent Number: 6,135,146
[45] Date of Patent: Oct. 24, 2000

[54] AUTOMATIC FAUCET DEVICE FOR CLEANING HUMAN BODY WITH OZONE-WATER

[75] Inventors: Akihisa Koganezawa; Yukio Akahori, both of Shizuoka, Japan

[73] Assignee: Take-One Office, Ltd., Tokyo, Japan

[21] Appl. No.: 09/307,729

[22] Filed: May 10, 1999

[30] Foreign Application Priority Data

Jul. 6, 1998 [JP] Japan .................................. 10-190295

[51] Int. Cl.[7] .................................................. F16K 37/00
[52] U.S. Cl. .................... 137/554; 137/551; 137/624.12; 251/129.04
[58] Field of Search .................................. 137/551, 554, 137/624.12; 251/129.04

[56] References Cited

U.S. PATENT DOCUMENTS

| | | | |
|---|---|---|---|
| 5,694,653 | 12/1997 | Harald | 4/623 |
| 5,855,356 | 1/1999 | Fait | 251/129.04 |
| 5,868,311 | 2/1999 | Cretu-Petra | 236/12.12 |
| 5,975,124 | 11/1999 | Stevens, II | 137/392 |
| 5,979,500 | 11/1999 | Jahrling et al. | 137/624.12 |

*Primary Examiner*—A. Michael Chambers
*Assistant Examiner*—Thomas L. McShane
*Attorney, Agent, or Firm*—Wenderoth, Lind & Ponack, L.L.P.

[57] ABSTRACT

An automatic faucet device capable of cleaning and sterilizing a human body of a user with no stress given to the user. The device includes: a water supply head; a first solenoid valve interposed in the course of a pipe connecting the water supply head to a pre-cleaning water source; a second solenoid valve interposed in the course of a pipe connecting the water supply head to an ozone-water source; and a sensor for detecting the presence of a substance such as a hand of a human body under a discharge port of the water supply head. The first solenoid valve is opened for a specific period of time A in response to a signal detected by the sensor, and the second solenoid valve is opened for a specific period of time C after an elapse of a specific period of time B since starting of the opening of the first solenoid valve. A graphic indicator including arrays of LEDs, which is disposed on the upper surface of the water supply head, controls the turn-on/off of the arrays of light emitting diodes in cooperation with the solenoid valve control means and schematically, graphically indicating both an elapsed time within the specific period of time B and an elapsed time within the specific period of time C.

9 Claims, 8 Drawing Sheets

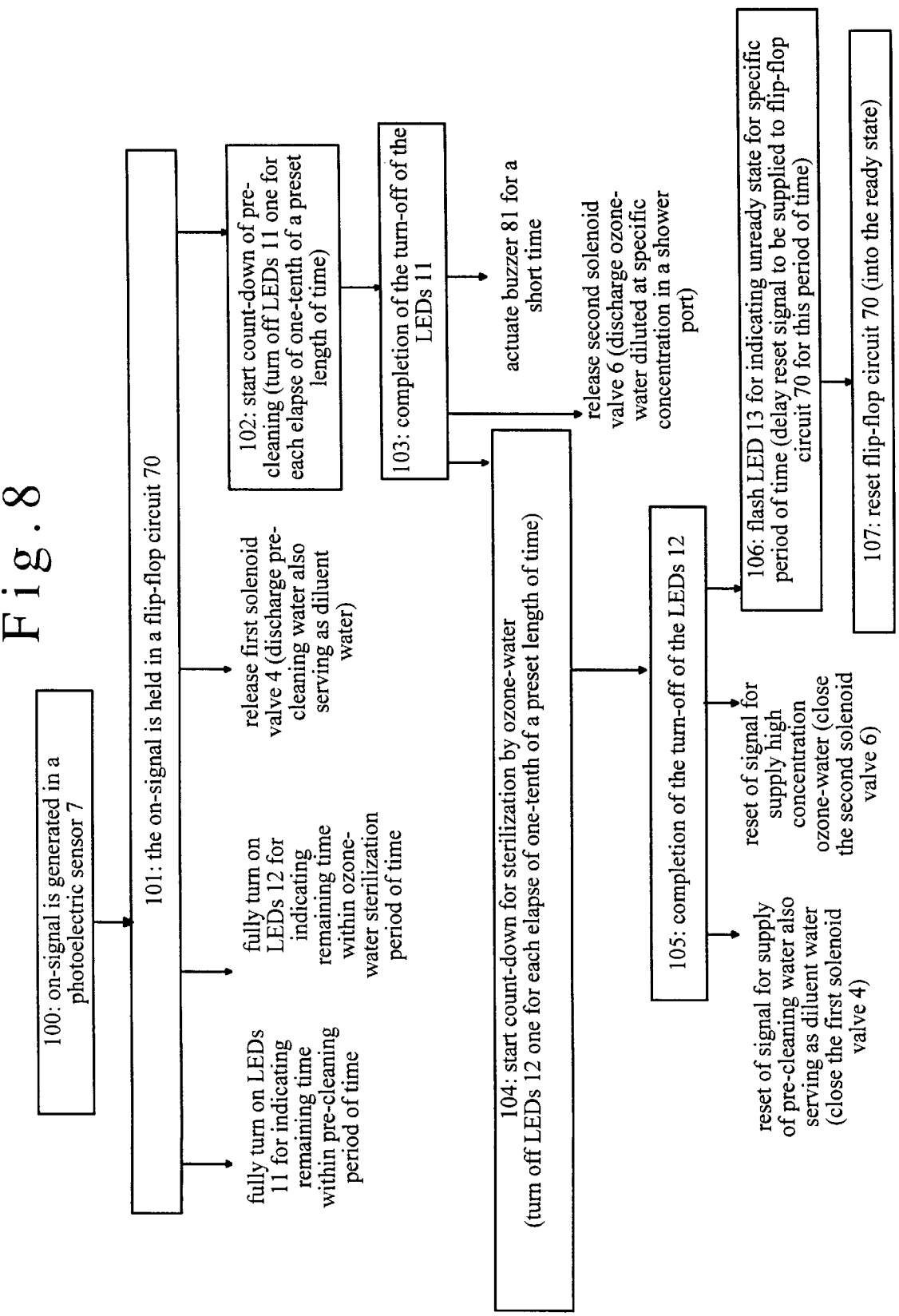

AUTOMATIC FAUCET DEVICE FOR CLEANING HUMAN BODY WITH OZONE-WATER

BACKGROUND OF THE INVENTION

1. Field of the Invention

The present invention relates to an automatic faucet device for cleaning a human body such as hands or feet with ozone-water for sterilization in working sites of the medical care, public health and food industry and in domestic houses, and particularly to an automatic faucet device for performing pre-cleaning of a human body with water and subsequently, automatically performing sterilization of the human body by contact of the human body with ozone-water for a specific period of time.

2. Description of the Related Arts

As a cleaning device making use of the sterilizing effect of ozone-water, a hand wash basin type used for working sites of the medical care has been known, for example, in Japanese Utility Model Laid-open No. Sho 63-42294. However, it is difficult to obtain a sufficient sterilizing effect by cleaning using ozone-water only in a small amount. In particular, in the case of cleaning a human body having contamination such as sebum and body fluid other than bacteria to be sterilized, a large amount of ozone is consumed to remove the contamination from the human body. In this case, since the degree of contamination is not specified, it is difficult to set a quantitative sterilization standard. Such a problem has been already appointed, for example, in Japanese Patent Laid-open No. Hei 7-108056. Another problem is that if a human body is cleaned with ozone water in a large amount or at a high concentration to obtain a sufficient sterilizing effect, there may occur a fear that the strong oxidizing force of ozone-water exerts adverse effect on the skin and the like of the human body.

To cope with these problems, there has been known a method of pre-cleaning a human body with usual water or a surface active agent to remove contamination adhering on the surface of the human body up to an allowable level and then bringing the human body into contact with ozone-water having a concentration in the order of several ppm for a specific period of time. This method is also taught in the above document, Japanese Patent Laid-open No. Hei 7-108056.

Incidentally, a number of persons are accustomed to cleaning using usual water or a surface active agent, and particularly persons at working sites of the medical care are sufficiently skillful in such cleaning, and accordingly, even if the contents (such as the utilization amount of the surface active agent and the like) of the pre-cleaning are entrusted to the user, a relatively constant cleaning effect should be achieved. However, in the present circumstances, a number of persons are not skillful in the sterilizing manner using ozone-water. Even in the case where a human body is stuck with less contamination in appearance, the human body should be pre-cleaned before cleaning using ozone water for obtaining a sufficient sterilizing effect by the cleaning using ozone-water; however, most of persons busy with tasks, for example, in hospitals are forgetful of the meaning of the pre-cleaning. On the other hand, there may often occur inconveniences that some persons forget the use of ozone-water after cleaning using a usual surface active agent or the like; forget to check the starting time of sterilization by ozone-water and fail to confirm, in the course of sterilization, a remaining time within the sterilization period of time; and stop the use of ozone-water in the middle of sterilization resulting from misunderstanding of the period of time required for sterilization by ozone-water. In such circumstances, the sterilization level may be varied against the users' will and a large stress may be given to the users in cleaning using ozone-water.

SUMMARY OF THE INVENTION

An object of the present invention is to provide an automatic faucet device, which is configured to perform pre-cleaning and subsequently, automatically perform sterilization by ozone-water so as to promote the thoroughness of a specific sterilizing level, and which includes a specific function of informing the user of the state of cleaning, that is, of causing the user to easily understand whether the present cleaning state is pre-cleaning or sterilization cleaning and also causing the user to sensorially understand a remaining time within each cleaning period of time, thereby enabling cleaning/sterilization of a human body with no stress given to the user.

To achieve the above object, according to the present invention, there is provided an automatic faucet device for cleaning a human body with ozone-water, including: a water supply head disposed over a sink; a first solenoid valve interposed in the course of a pipe connecting the water supply head to a pre-cleaning water source; a second solenoid valve interposed in the course of a pipe connecting the water supply head to an ozone-water source; a sensor for detecting the presence of a substance like apart of a human body, for example, a hand, under a discharge port of the water supply head; a solenoid valve control means for opening the first solenoid valve for a specific period of time A in response to a signal detected by the sensor, and opening the second solenoid valve for a specific period of time C after an elapse of a specific period of time B since starting of the opening of the first solenoid valve; a graphic indicator including arrays of light emitting diodes, the indicator being disposed at such a position as to allow a user of the water supply head to take a look at the indicator; and an indication control means for controlling the turn-on/off of the arrays of light emitting diodes in cooperation with the solenoid valve control means and discriminably, graphically indicating both an elapsed time within the specific period of time B and an elapsed time within the specific period of time C after starting of the opening of the first solenoid valve.

The above device preferably further includes a buzzer for generating an alarm sound to the user; and a buzzer driving means for actuating the buzzer for a short period of time near a point of time when the second solenoid valve is opened.

The specific period of time A is preferably set to be nearly equal to the sum of the specific period of time B and the specific period of time C.

The graphic indicator is preferably disposed on an upper surface portion of the water supply head.

The graphic indicator preferably has a first written character portion indicating that there is a pre-cleaning period of time, the first portion being annexed to a graphic portion indicating the elapsed time within the specific period of time B; and a second written character portion indicating that there is an ozone-water sterilization period of time, the second portion being annexed to a graphic portion indicating the elapsed time within the specific period of time C.

The device preferably further includes a means for turning-on a lamp for informing the user of unready state of the device for a specific period of time after closing of the second solenoid valve.

The device preferably further includes a time-setting means for arbitrarily varying each of the specific period of time B and the specific period of time C.

The automatic faucet device according to the present invention causes or leads a number of users who may often have an aversion to time restriction due to the two-stage cleaning manner including pre-cleaning and sterilization cleaning to easily understand the necessity of both of the cleaning stages and to sensorially, easily recognize the progress of each cleaning stage and the remaining time within each cleaning stage with sounds and graphs, rather than with theory and numeral values. The automatic faucet device, therefore, has a remarkably good effect in reducing the stress given to the user and in promoting the thoroughness of a specific sterilization level.

BRIEF DESCRIPTION OF THE DRAWINGS

An automatic faucet device according to the present invention is illustrated schematically in the accompanying drawings in which:

FIG. 8 is a flow chart showing operation of the automatic faucet device shown in FIG. 1.

DETAILED DESCRIPTION OF THE PREFERRED EMBODIMENTS

Figure 1:
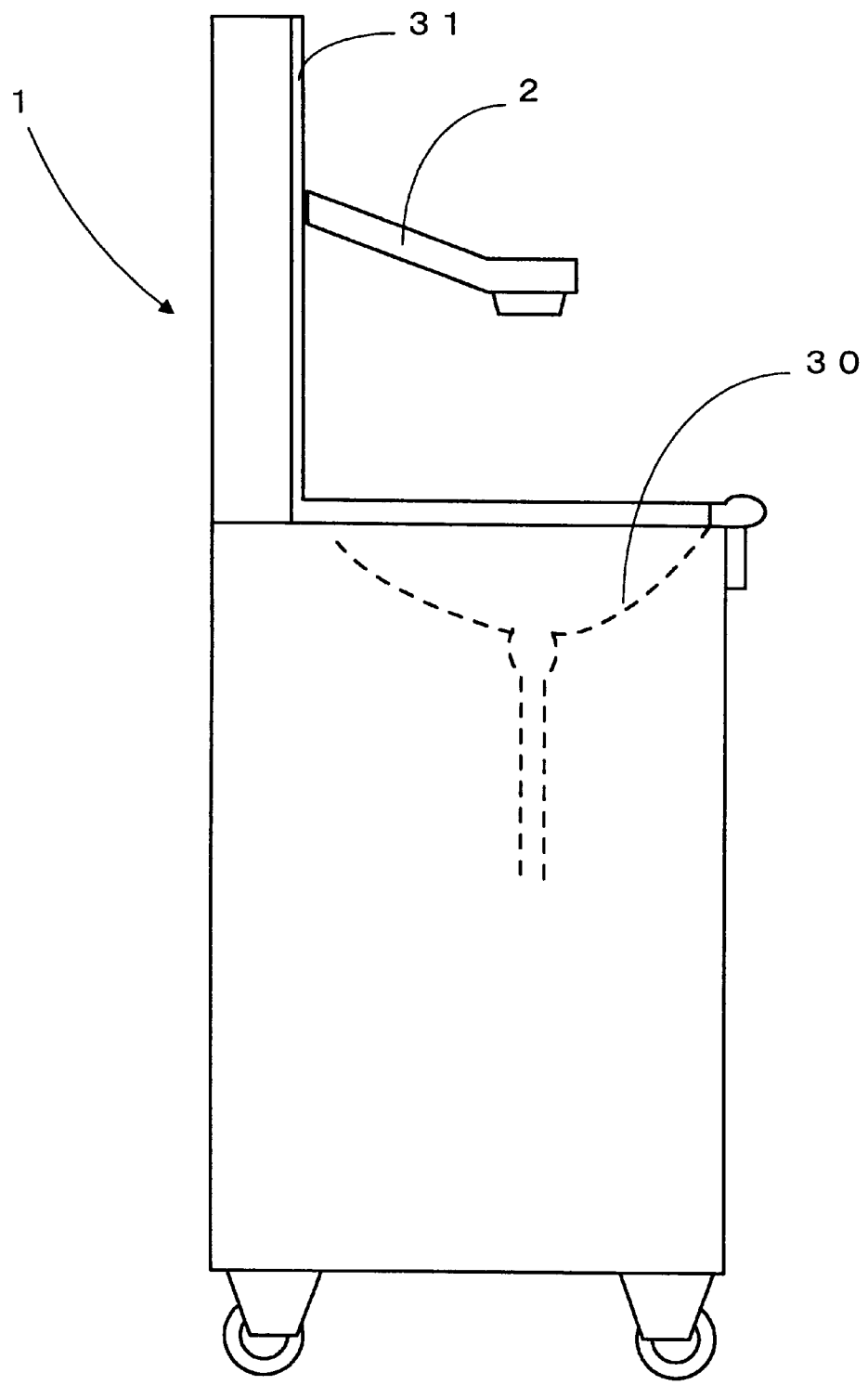
FIG. 1 is a schematic side view of an automatic faucet device according to one embodiment of the present invention.

A schematic side view of an automatic faucet device 1 applied to a hand-wash basin as one embodiment of the present invention is shown in FIG. 1. The automatic faucet device 1 generally includes a sink 30 for defining a wash place, a water supply head 2 disposed over the sink 30, and a wall surface 31 for supporting the water supply head 2.

Figure 2:
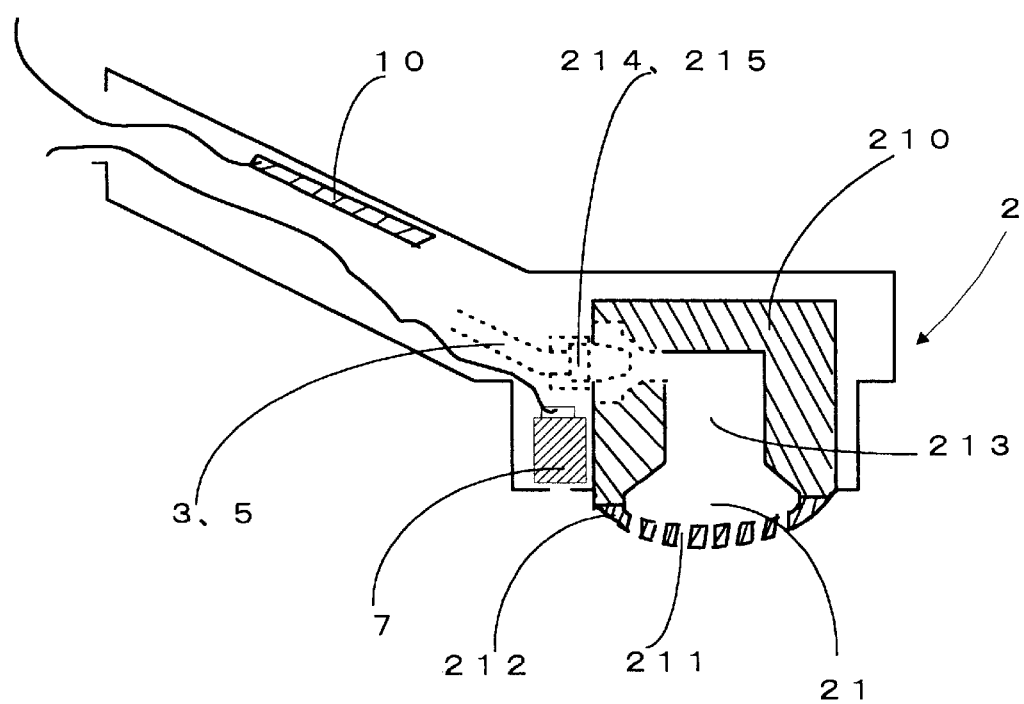
FIG. 2 is a vertical sectional view of a water supply head of the automatic faucet device shown in FIG. 1.
Figure 3:
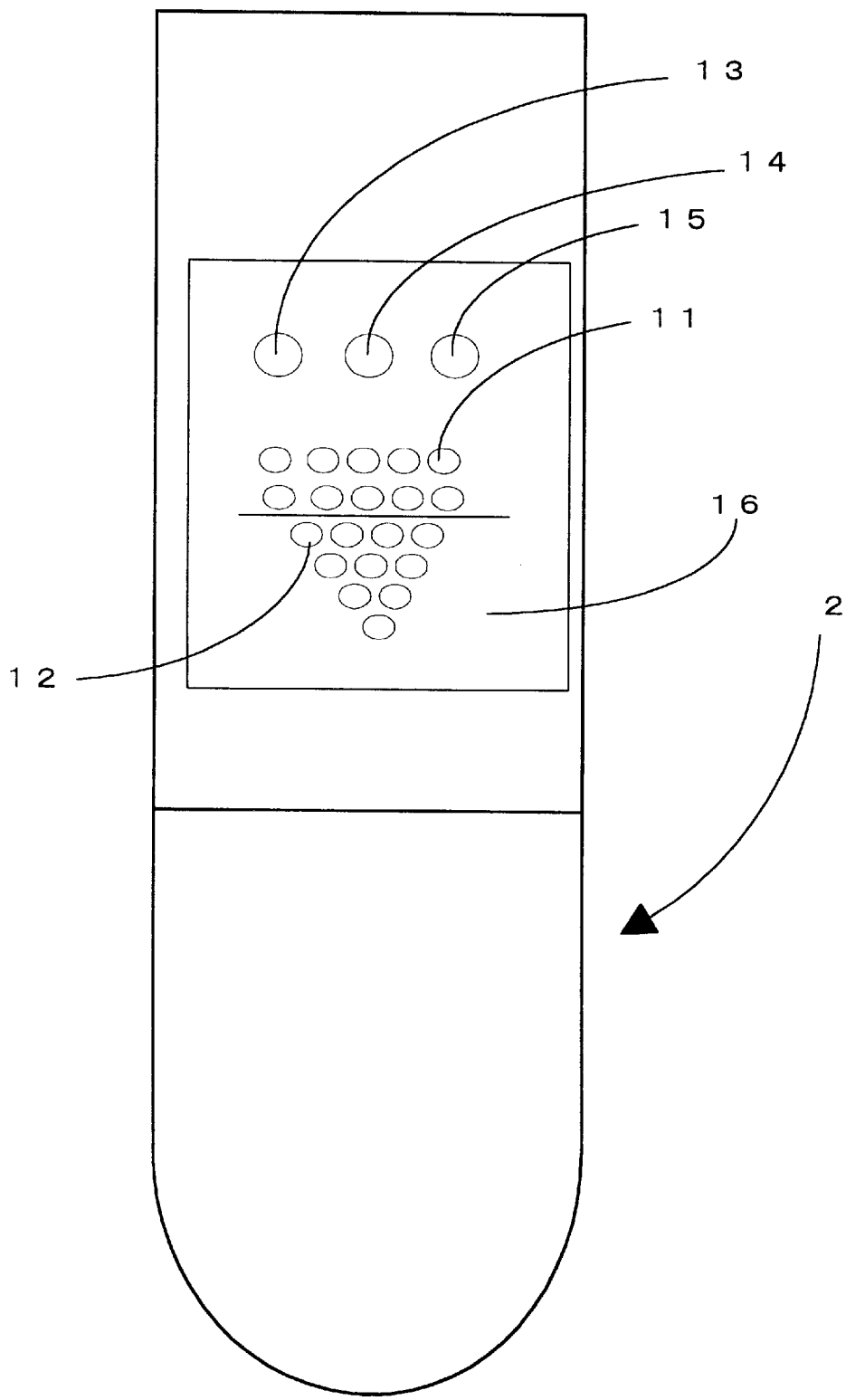
FIG. 3 is a plan view of the water supply head shown in FIG. 2.
Figure 4:
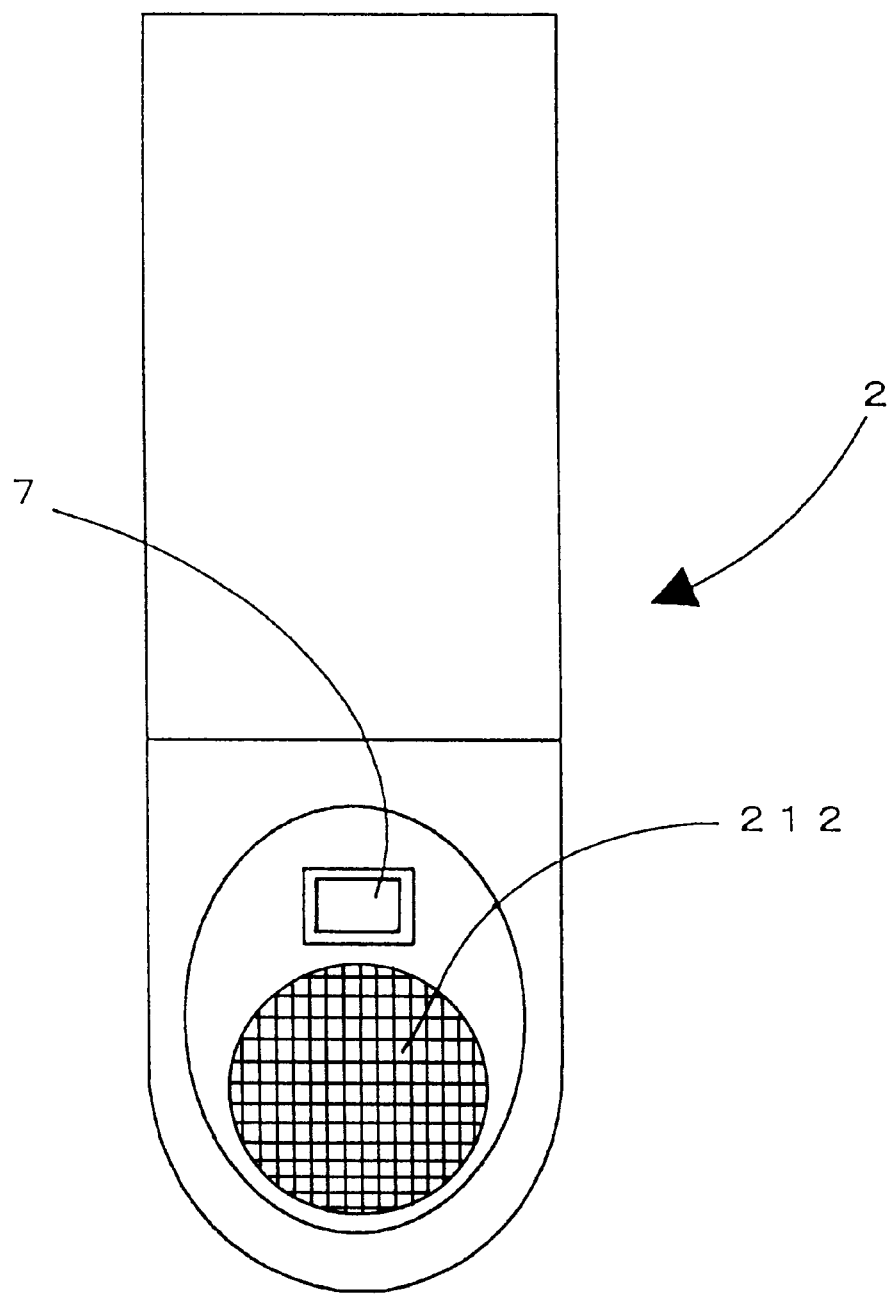
FIG. 4 is a bottom view of the water supply head shown in FIG. 2.

The water supply head 2 has, as shown by the vertical sectional view of FIG. 2, a corrosion-resisting resin made core 210. The core 210 defines a discharge port 21 opened substantially downwardly for discharging water for pre-cleaning and ozone-water for sterilization. As shown in the plan view of FIG. 3 in addition to FIG. 2, the water supply head 2 includes an indicator 10 for visual indication by means of light emitting diodes (LEDs). In consideration of the natural visual line of the user, the indicator 10 is disposed at such a position as to allow the user to take a look at the indicator 10 substantially from the front, obliquely upward side. As shown in the bottom view of FIG. 4 in addition to FIG. 2, a sensor 7 is disposed in the vicinity of the discharge port 21 of the head 2. If the user standing in front of the device stretches out his hands under the discharge port 21, the hands are detected by the sensor 7. The sensor 7 is preferably configured as a proximity sensor of a non-contact type with no reflection plate, for example, a diffuse reflection type photoelectric sensor.

Figure 5:
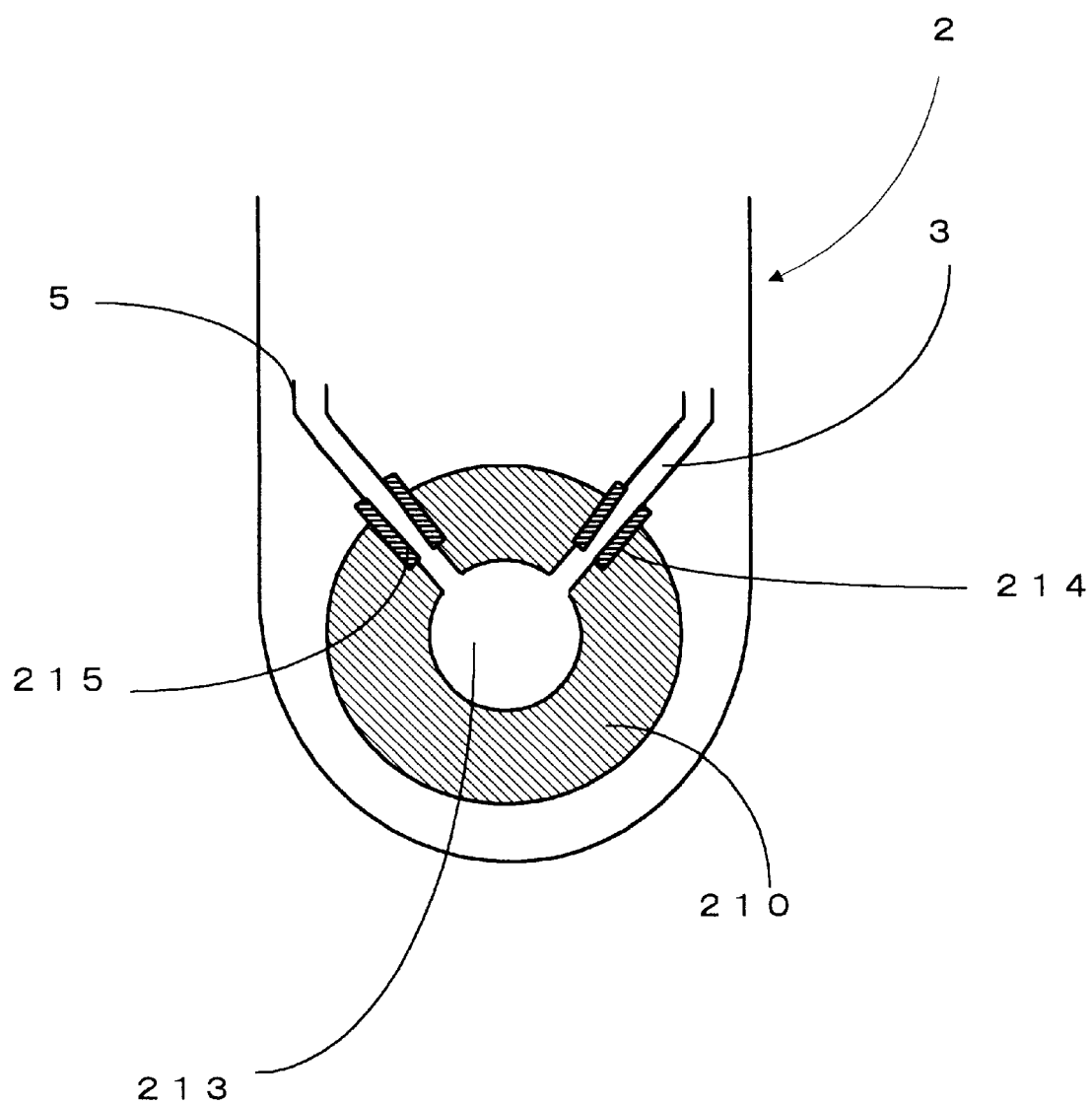
FIG. 5 is a schematic horizontal sectional view of the water supply head shown in FIG. 2.

A cover 212, which has a number of small openings 211 for changing a stream of water discharged from the discharge port 21 into a shower of water, is preferably mounted to the core 210 in such a manner as to cover the discharge port 21. The cover 212 is preferably made of corrosion-resisting resin. The corrosion-resisting resin for forming each of the core 210 and the cover 212 may be selected from suitable kinds of hard vinyl chloride; however, if an emphasis is put on a strong corrosion resistance against ozone, a fluorocarbon resin is preferably used as the corrosion-resisting resin. The core 210, more preferably, contains a diluting space 213. As will be described later, ozone-water at a higher concentration than that of ozone-water to be discharged for sterilization is supplied into the diluting space 213, and is diluted with water at the diluting space 213. As shown by the schematic horizontal sectional view of FIG. 5, the diluting space 213 is communicated to a pipe 3 connected to a pre-cleaning water source and to a pipe 5 connected to a ozone water source. The pipe 3 is mounted in the core 210 via a coupling 214 and the pipe 5 is mounted in the core 210 via a coupling 215. In consideration of the required degree of properties such as corrosion resistance, material strength, and adhesive force, the pipe 3 may be made from an inexpensive resin such as polyethylene and the coupling 214 may be made from an inexpensive resin such as polypropylene; however, each of the pipe 5 and coupling 215 may preferably be made from a fluorocarbon resin.

The formation and arrangement of the indicator 10 will be described below. A plurality of LEDs are supported on the inner space of the water supply head 2. Openings corresponding to the plurality of LEDs are formed in the upper surface portion, tilted forwardly, of the water supply head 2. A transparent or semi-transparent cover 16 is stuck from outside in such a manner as to cover the openings. The cover 16 protects permeation of external dust and water drops into the openings, and allow light rays emitted from the LEDs to pass therethrough to the outside and to be recognized by the user. It should be noted that a portion, not covering each opening, of the cover 16 may be of course opaque. The plurality of LEDs preferably include a LED 13 for indicating ready/unready state of the automatic faucet device 1, a LED 14 for indicating occurrence of an error, a LED 15 for indicating the on-state of a power supply, a LED array 11 for graphically indicating a remaining time in a pre-cleaning period of time, and a LED array 12 for graphically indicating a remaining time in an ozone-water sterilization period of time. At least the LED array 11 and LED array 12 are preferably color-coded for easy discrimination from each other. On the cover 16 of the indicator 10, suitable characters for indicating the meaning of each of the LEDs and LED arrays are written and also suitable lines for separating the LEDs and LED arrays from each other are drawn as needed. Of course, these characters and lines may be written and drawn on the upper surface of the head 2 under the cover 16. In this case, these characters and lines are viewed by the user via the cover 16.

Figure 6:
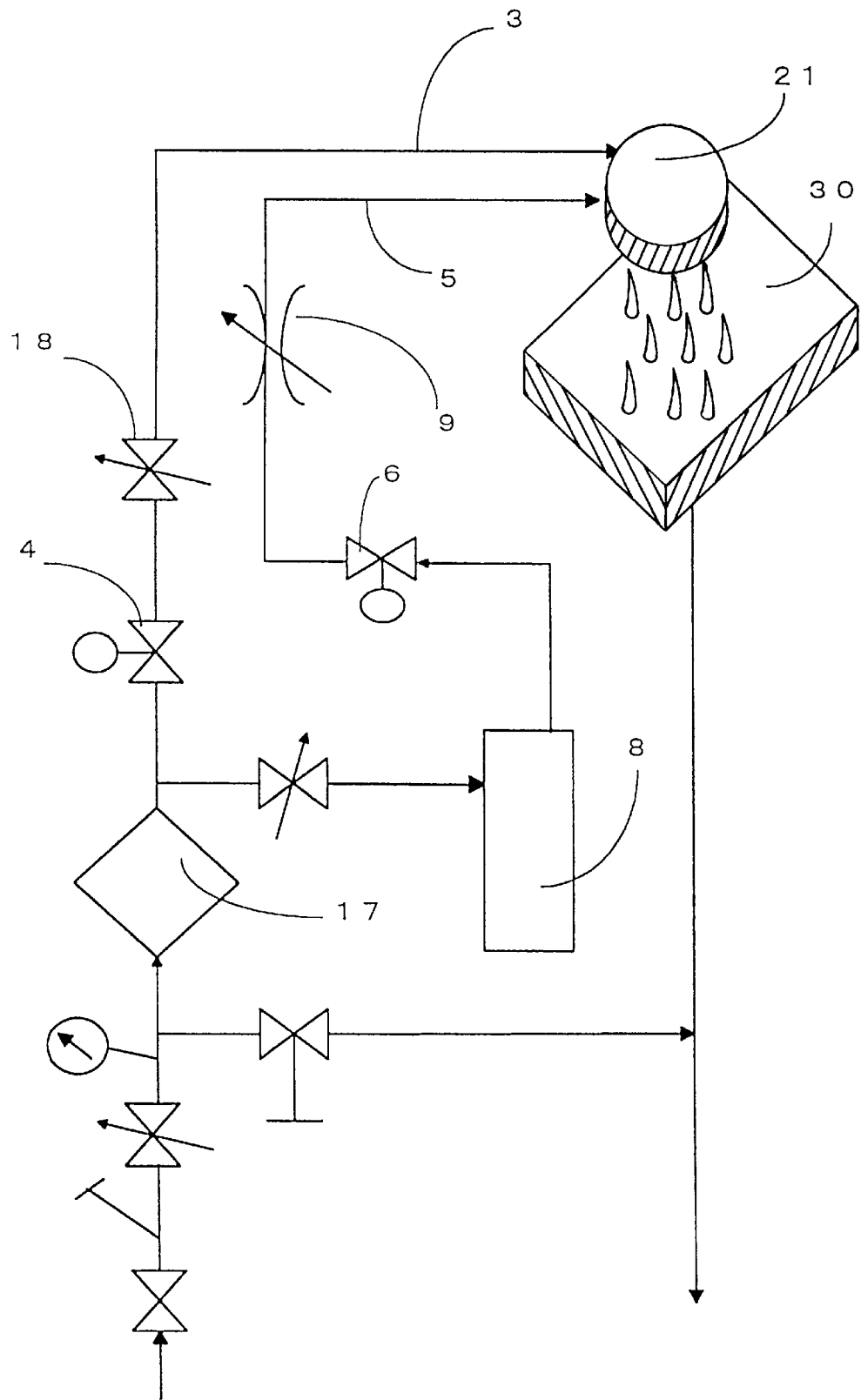
FIG. 6 is a distribution diagram of piping system of the automatic faucet device shown in FIG. 1.

The pipe 3 has a first solenoid valve 4 which is interposed between the core 210 and the pre-cleaning water source. The pre-cleaning water source may be a usual public water-supply or an independent water tank. In accordance with the quality and pressure of water supplied from the pre-cleaning water source, the pipe 3 has, as shown in FIG. 6, known means for improving the water quality, adjusting the water pressure and regulating the flow rate of water, such as a pressure reduction valve, a filter 17 using suitable activated carbon, a flow regulating valve 18, and a bypassing line; and the pipe 3 further has a monitoring means. The pipe 5 for ozone-water has a second solenoid valve 6 which is interposed between the core 210 and an ozone-water source 8. The ozone-water source 8 may be a tank for storing ozone-water produced in another location, but further preferably, it may be configured as an ozone-water producing apparatus for producing ozone-water using a quality-improved water. This quality-improved water may be supplied by a branch line from the pipe 3 as shown in FIG. 6. As a method of producing ozone-water, there have been known methods, for example, a method of producing ozone in water by electrolysis of water, and a method of producing ozone gas by electric discharge in oxygen gas and dissolving the ozone gas in water. In this embodiment, there may be adopted a method selected from those known methods and, in necessary, suitably adapted or improved. At the ozone-water source 8, the ozone-water thus produced is preferably circulated for improving or keeping the concentration of the ozone-water. In this case, the ozone-water can be supplied to the solenoid valve 6 by making use of the circulating pressure. The pipe 5 preferably includes a needle valve 9 for adjusting the setting flow rate of ozone-water.

Figure 7:
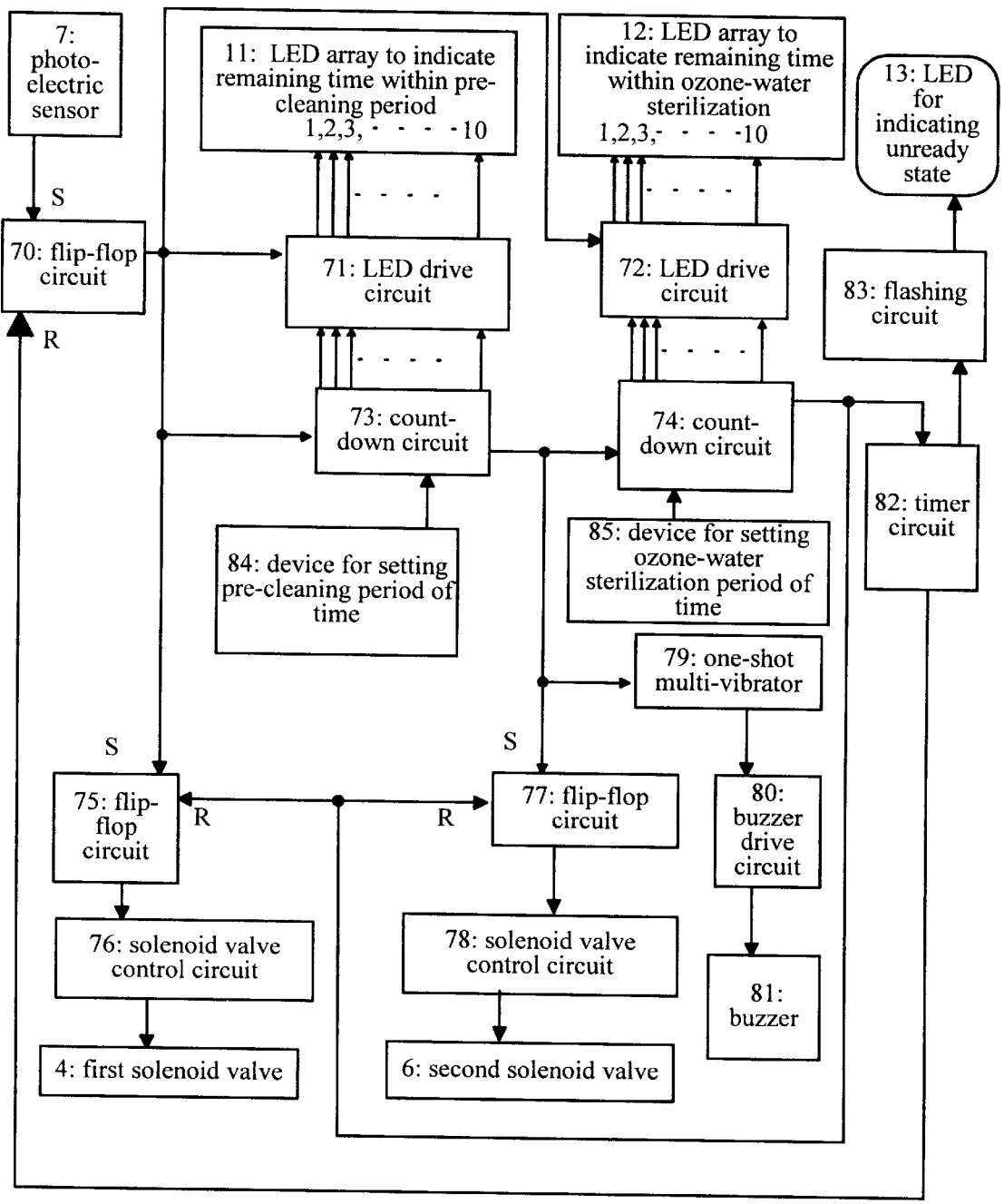
FIG. 7 is a distribution diagram of control circuits used for the automatic faucet device shown in FIG. 1.

A control unit (not shown) of the automatic faucet device 1 has a configuration and a connection structure shown by the circuit diagram of FIG. 7. The output line of a flip-flop circuit 70 connected to a signal output line of the sensor 7 is connected to a drive circuit 71 for driving the LED array 11, a count-down circuit 73 for outputting the count-down state to the drive circuit 71, a drive circuit 72 for driving the LED array 12, and another flip-flop circuit 75. The count-down circuit 73 drives the LED array 11 in such a manner that the LEDs of the number corresponding to a count-down time are turned off. The flip-flop circuit 75 has an output line connected to a solenoid valve control circuit 76 for driving the solenoid valve 4 provided in the pre-cleaning water pipe 3.

An output indicating the completion of the count-down performed in the count-down circuit 73 is supplied to another count-down circuit 74, a further flip-flow circuit 77 and a one-shot multi-vibrator 79. The count-down circuit 74 outputs a count-down state to the drive circuit 72 and drives the LED array 12 in such a manner that the LEDs of the number corresponding to the count-down time are turned off. The flip-flop circuit 77 has an output line connected to a solenoid valve control circuit 78 for driving the second solenoid valve 6. The one-shot multi-vibrator 79 has an output line connected to a buzzer drive circuit 80 for driving a buzzer 81. When the count-down performed in the count-down circuit 73 is completed, the buzzer drive circuit 80 actuates the buzzer 81 for a short period of time. The output indicating the completion of the count-down performed in the count-down circuit 74 is supplied to a timer circuit 82 to trigger the timer circuit 82 and is also supplied to the flip-flop circuits 75 and 77 to reset the flip-flop circuits 75 and 77. After an elapse of a predetermined specific delay time since the triggering of the timer circuit 82, the output of the timer circuit 82 is supplied to the flip-flop circuit 70 to rest the flip-flop circuit 70. During the timer operation of the timer circuit 82, an operational signal is outputted from the timer circuit 82 to a flashing circuit 83 for flashing the LED 13 for indicating the unready state of the device 1. Preferably, the control unit of the automatic faucet device 1 is provided with a setting device 84 for adjusting the pre-cleaning period of time B by adjusting the setting value of the count-down circuit 73, and a setting device 85 for adjusting the ozone-water sterilization period of time C by adjusting the setting value of the count-down circuit 74. It should be noted that circuits for driving the error indicating LED 14 and power supply indicating LED 15 among the components constituting the indicator 10 are not shown in FIG. 7; however, it should be easily carried out by a person skilled in the art to additionally provide these circuits with reference to the circuit diagram of FIG. 7.

Finally, the operation of the automatic faucet device 1 will be described with reference to FIG. 8. FIG. 8 is a schematic flow chart showing the operational control of the automatic faucet device 1. When the hands of the user are held near the lower port of the water supply head 2, the photoelectric sensor 7 generates an on-signal (step 100), and the on-signal of the photoelectric sensor 7 is held in the flip-flop circuit 70 (step 101). In such a state, the LED array 11 for indicating the remaining time in the pre-cleaning period of time is full turned on, the LED array 12 for indicating the remaining time in the ozone-water sterilization period of time is also full turned on, and the solenoid valve 4 for pre-cleaning water is released to discharge pre-cleaning water from the discharge port 21. The pre-cleaning water is thus made contact with the hands of the user, thereby starting the pre-cleaning. At the same time, the count-down for pre-cleaning begins (step 102). In accordance with the count-down, the ten LEDs of the LED array 11 are turned off in sequence one for each elapse of one-tenth of the pre-cleaning period of time B. When the count-down is completed and the ten LEDs of the LED array 11 for pre-cleaning are all turned off (step 103), the buzzer 81 is actuated for a specific short period of time to inform the user of starting of sterilization by ozone-water, and the solenoid valve 6 for ozone-water is released to discharge ozone-water from the discharge port 21. The ozone-water is thus made contact with the hands of the user, thereby starting the sterilization by ozone-water. Preferably, ozone-water supplied through the pipe 5 is diluted with water supplied through the pipe 3 at the diluting space 213 defined by the core 210 and the cover 212, and is then sent out into the form of a shower via the shower cover 212. That is to say, water for pre-cleaning is continued to be discharged and is used as water for dilution. It should be noted that the dilution ratio is previously set by the flow regulating means 9 and 18, and the like.

The count-down for sterilization by ozone-water begins simultaneously with release of the solenoid valve 6 (step 104). In accordance with the count-down, the LEDs of 10 pieces of the LED array 12 are turned off in sequence one for each elapse of one-tenth of the ozone-water sterilization period of time C. When the count-down is completed and the LEDs of the LED array 12 for sterilization by ozone-water are all turned off (step 105), a reset signal is supplied to each of the flip-flop circuits 75 and 77 to close the solenoid valves 6 and 4, and the timer circuit 82 is operated to flash the LED 13 for indicating the unready state (step 106). After that, a reset signal is supplied to the flip-flop circuit 70 (step 107). That is to say, at step 106, the timer circuit 82 delays the reset of the sensor signal by, for example, about 3 sec in order to prevent the next pre-cleaning from being erroneously started even if the hands of the user having been already subjected to sterilization go in and out of the detecting range of the sensor 7 within the above delay time.

As described above, the automatic faucet device according to this embodiment has the following configuration. The first solenoid valve 4 is opened in response to the detection signal from the sensor 7 for a specific period of time A equal to the sum of the pre-cleaning period of time B and the ozone-water sterilization period of time C, and the second solenoid valve 6 is opened for the specific period of time C after an elapse of the specific period of time B since starting of the opening of the first solenoid valve 4. In this embodiment, the pre-cleaning period of time B is generally set at a value ranging from 7 to 30 sec and the user may use a surface active agent in combination with water, while the ozone-water sterilization period of time C is generally set at a value ranging from 15 to 30 sec assuming that the concentration of ozone-water is set at 4 ppm (in the case of using ozone-water for 30 sec, the discharged amount of ozone-water is substantially set at a value ranging from 0.75 to 1.25 liters) The graphic indicator 10 including the LED arrays arranged on the upper surface of the water supply head 2 controls the turn-on/off of the LED arrays in cooperation with the means for controlling the solenoid valves, and schematically, graphically indicates the elapsed time within the specific period of time B and the elapsed time within the specific period of time C.

While the preferred embodiments of the present invention have been described, such description is for illustrative purposes only, and it is to be understood that changes and variations may be made without departing from the spirit or scope of the following claims.

We claim:

1. An automatic faucet device for cleaning a human body with ozone-water, comprising:
    a water supply head disposed over a sink;
    a first solenoid valve interposed in the course of a pipe connecting said water supply head to a pre-cleaning water source;
    a second solenoid valve interposed in the course of a pipe connecting said water supply head to an ozone-water source;
    a sensor for detecting the presence of a substance like a part of a human body under a discharge port of said water supply head;
    a solenoid valve control means for opening said first solenoid valve for a specific period of time A in response to a signal detected by said sensor, and opening said second solenoid valve for a specific period of time C after an elapse of a specific period of time B since starting of the opening of said first solenoid valve;
    a graphic indicator including arrays of light emitting diodes, said indicator being disposed at such a position as to allow a user of said water supply head to take a look at said indicator; and
    an indication control means for controlling the turn-on/off of said arrays of light emitting diodes in cooperation with said solenoid valve control means and discriminably, graphically indicating both an elapsed time within the specific period of time B and an elapsed time within the specific period of time C after starting of the opening of said first solenoid valve.

2. An automatic faucet device according to claim 1, further comprising:
    a buzzer for generating an alarm sound to the user; and
    a buzzer driving means for actuating said buzzer for a short period of time near a point of time when said second solenoid valve is opened.

3. An automatic faucet device according to claim 1, wherein the specific period of time A is set to be nearly equal to the sum of the specific period of time B and the specific period of time C.

4. An automatic faucet device according to claim 2, wherein the specific period of time A is set to be nearly equal to the sum of the specific period of time B and the specific period of time C.

5. An automatic faucet device according to claim 1, wherein said graphic indicator is disposed on an upper surface portion of said water supply head.

6. An automatic faucet device according to claim 1, wherein said graphic indicator has a first written character portion indicating that there is a pre-cleaning period of time, said first written character portion being annexed to a graphic portion indicating the elapsed time within the specific period of time B; and a second written character portion indicating that there is an ozone-water sterilization period of time, said second written character portion being annexed to a graphic portion indicating the elapsed time within the specific period of time C.

7. An automatic faucet device according to claim 2, wherein said graphic indicator has a first written character portion indicating that there is a pre-cleaning period of time, said first written character portion being annexed to a graphic portion indicating the elapsed time within the specific period of time B; and a second written character portion indicating that there is an ozone-water sterilization period of time, said second written character portion being annexed to a graphic portion indicating the elapsed time within the specific period of time C.

8. An automatic faucet device according to claim 1, further comprising a means for turning-on a lamp for informing the user of unready state of said device for a specific period of time after closing of said second solenoid valve.

9. An automatic faucet device according to claim 1, further comprising a time-setting means for arbitrarily varying each of the specific period of time B and the specific period of time C.

* * * * *